US00PP08816P

United States Patent [19]

Stravers

[11] Patent Number: Plant 8,816

[45] Date of Patent: Jul. 5, 1994

[54] *GERBERA JAMESONII* PLANT NAMED TEREEUW

[75] Inventor: Lambertus J.M. Stravers, Carlsbad, Calif.

[73] Assignee: Terra Nigra B.V., De Kwakel, Netherlands

[21] Appl. No.: 116,620

[22] Filed: Sep. 7, 1993

[51] Int. Cl.[5] ..... A01H 5/00
[52] U.S. Cl. ..... Plt./68.1
[58] Field of Search ..... Plt. 68.1

*Primary Examiner*—James R. Feyrer

[57] ABSTRACT

A new and distinct cultivar of Gerbera plant named 'Tereeuw', characterized by its semi-double type, a distinct warm yellow ray floret which is a solid yellow color throughout, a very distinctive green disc floret, the outermost florets of which display yellow stigmas and the middle flowers of which show yellow anthers, yellow perianth lobe color and 120 mm overall flower diameter.

1 Drawing Sheet

BACKGROUND OF THE INVENTION

The present invention comprises a new and distinct cultivar of *Gerbera jamesonii*, referred to by the cultivar name 'Tereeuw'. 'Tereeuw' was originated from a hybridization program in De Kwakel, The Netherlands in 1991. The female parent was 'Geel 1', and the male parent was 'Tamara'. The female parent 'Geel 1' differs from 'Tereeuw' by its singleness, having a less warm color and a better vase-life. 'Geel 1' has not been patented in the United States. Moreover, it was not available to others outside the company. The male parent 'Tamara' is a commercial variety of another breeding company. It is unknown to me if this variety has been patented in the United States. 'Tamara' is patented in the Netherlands and is available to others. 'Tamara' differs from 'Tereeuw' by its color intensity of the ray flowers which is not as clear yellow as 'Tereeuw', and it differs especially by the color of the disc floret which doesn't have the same distinctive color green as 'Tereeuw'. The new cultivar was selected by me from the progeny of the stated parentage on or about November 1991. The first asexual reproduction of 'Tereeuw' was accomplished when vegetative cuttings for tissue culture initiation were taken on December 1991 in De Kwakel, The Netherlands. The new cultivar is presently being propagated by cuttings and tissue culture. Horticultural examination of selected units initiated December 1991 has demonstrated that the combination of characteristics as herein disclosed for 'Tereeuw' are firmly fixed and are retained through successive generations of asexual reproduction.

The following observations, measurements and comparisons describe plants grown in De Kwakel, The Netherlands, under greenhouse conditions which closely approximate those generally used in commercial practice. The following traits have been repeatedly observed and are determined to be basic characteristics of 'Tereeuw', which in combination distinguish this Gerbera from its parents and all other varieties of which I am aware:

A.

1. *Type.*—Semi-double.
2. *Color of ray floret.*—Distinctive yellow.
3. *Color of disc floret.*—Very distinctive green.
4. *Color of perianthy lobe.*—Yellow.

5. *Diameter of flower head.*—Large 120 mm.

Of the many commercial cultivars known to me, there is no cultivar similar in comparison to 'Tereeuw'.

BRIEF DESCRIPTION OF THE FIGURE OF THE DRAWING

The accompanying photographic drawing shows typical inflorescence characteristics nearly true as possible. In the following description, color references are made to The Royal Horticultural Society Color Chart (RHS). The color values were determined at approximately 10:30 a.m. on 17 Jun. 1993 under natural light at De Kwakel.

BOTANICAL DESCRIPTION OF THE PLANT

Botanical: *Gerbera jamesonii* cv. Tereeuw.

INFLORESCENCE

A. Capitulum:
- *Form.*—Flat shaped.
- *Type.*—Semi-double.
- *Diameter across face.*—120 mm.

B. Corolla of ray florets:
- *Color (general tonality from a distance of 3 meters)*.—Yellow.
- *Color (topside)*.—Yellow RHS 14A.
- *Color (bottom)*.—Yellow RHS 14C.

C. Corolla of disc florets:
- *Color (mature)*.—Green RHS 145A.
- *Color (immature)*.—Green RHS 145A.

D. Reproductive organs:
- *Stigma.*—Yellow RHS 10B.
- *Anthers.*—Yellow RHS 13A.
- *Pappus.*—Yellow RHS 12D.

PLANT

A. General appearance:
- *Height.*—40 cm.

B. Foliage:
- *Color (abaxial)*.—Green RHS 137A.
- *Color (adaxial)*.—Green RHS 137A.
- *Shape.*—The angle of apex: right angle. The shape of apex: pointed. The margin of lobes: crenate.

C. Disease resistance: No special disease resistance.

OTHER CHARACTERISTICS

The following traits have been repeatedly observed and are determined to be basic characteristics of 'Tereeuw', which in combination distinguish this Gerbera as a new and distinct cultivar.

Leaf blade:

*Length.*—Long.
*Width.*—Medium.
*Thickness.*—Medium.
*Blistering.*—Medium.
*Pubescence.*—On upper side (midrib excluded): Medium.
*Depth of cuts or incisions in leaf.*—Basal part: Deep. Central part: Deep. Distal part: Shallow.
*Color.*—Upper side of the leaf blade is green (RHS 137B).
*Glossiness on upper side.*—Medium.
*Angle of apex.*—Right angle.
*Shape of apex.*—Pointed.
*Margin of lobes.*—Crenate.
*Extensions of margin.*—Medium.
*Petiole length.*—Long; 15 cm.
*Petiole anthocyanin coloration.*—Weak.

Peduncle:

*Length.*—Long (approx. 70 cm).
*Cross section.*—Elliptic.
*Tendency to fasciation.*—Present.
*Thickness.*—Medium.
*Strength.*—Medium.
*Pubescence.*—Medium.
*Color.*—Medium green.
*Anthocyanin coloration.*—At base: Medium. At top: Absent.
*Involucral bracts.*—Present.

Flower head:

*Type.*—Semi-double.
*Diameter.*—Large (approx. 120 mm).
*Involucre.*—Height: Medium (15 mm). Diameter: Medium (50 mm). Number of bracts: Medium (approx. 85). Longitudinal axis of bracts of inner rows: Straight. Anthocyanin: Absent. Pubescence: Medium.
*Ray florets.*—Number: Medium (approx. 60). Shape: Obovate. Longitudinal axis outer row: Reflexing. Longitudinal axis inner row: Straight.
*Outer ray florets.*—Cross section: Flat. Length: Medium (50 mm). Width: Medium. Longitudinal folding: Medium. Angle of apex: Right angle. Shape of apex: Pointed. Incisions of apex: Present. Number: two. Depth: medium. Length of free petals: Long. Color distribution on inner side: Uniform. Edge of different color: Absent. Striation: Absent. Claw spot: Absent.

Disc florets:

*Diameter.*—Medium 30–39 mm.
*Main color perianth lobes.*—Female flowers: Yellow (RHS 14A). Male flowers: Yellow (RHS 23B).

Reproductive parts:

*Stigma.*—Main color yellow (RHS 10B).
*Anthers.*—Main color yellow (RHS 13A).
*Pappus.*—Main color yellow (RHS 12D).
*Fertility.*—Very good; around 250 pollen. The plant will form viable seed very easily.

I claim:

1. A new and distinct cultivar of Gerbera plant named 'Tereeuw', as illustrated and described, characterized by its semi-double type, a distinct warm yellow ray floret which is a solid yellow color throughout, a very distinctive green disc floret, the outermost florets of which display yellow stigmas and the middle flowers of which show yellow anthers, yellow perianth lobe color and 120 mm overall flower diameter.

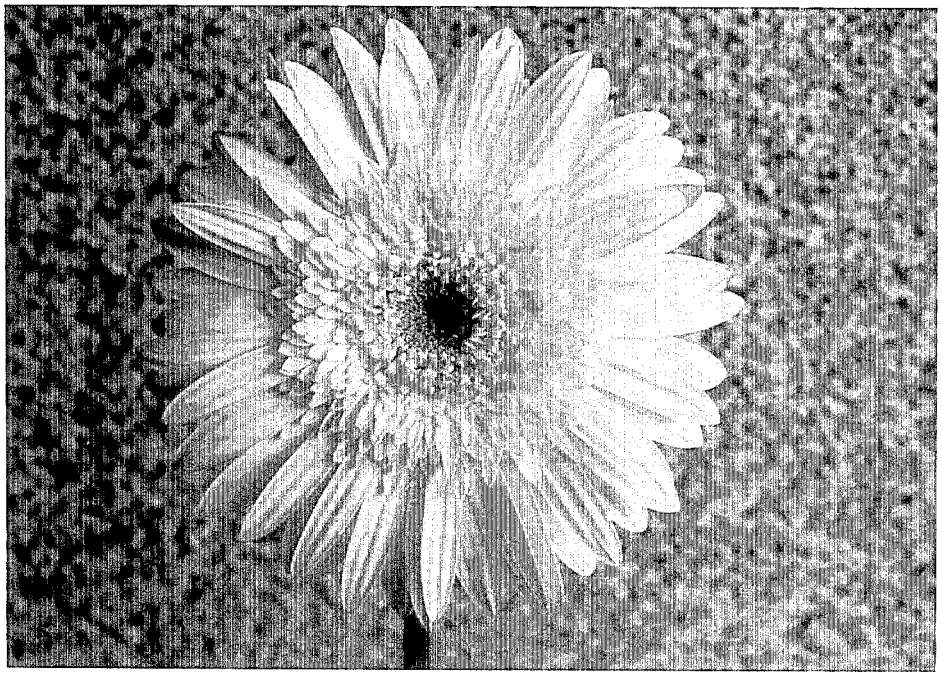

* * * * *